(12) United States Patent
Watanabe

(10) Patent No.: US 9,739,658 B2
(45) Date of Patent: Aug. 22, 2017

(54) CELL PEELING IDENTIFICATION DEVICE AND CELL PEELING IDENTIFICATION METHOD

(71) Applicant: SHIBUYA CORPORATION, Kanazawa-shi, Ishikawa (JP)

(72) Inventor: Daisuke Watanabe, Kanazawa (JP)

(73) Assignee: SHIBUYA CORPORATION, Kanazawa-shi, Ishikawa (JP)

( * ) Notice: Subject to any disclaimer, the term of this patent is extended or adjusted under 35 U.S.C. 154(b) by 0 days.

(21) Appl. No.: 14/926,967

(22) Filed: Oct. 29, 2015

(65) Prior Publication Data

US 2016/0123800 A1   May 5, 2016

(30) Foreign Application Priority Data

Oct. 31, 2014  (JP) ................. 2014-223571

(51) Int. Cl.
| | |
|---|---|
| *G06K 9/00* | (2006.01) |
| *G01J 1/42* | (2006.01) |
| *G01N 33/483* | (2006.01) |
| *G06T 7/00* | (2017.01) |
| *G06T 7/194* | (2017.01) |

(52) U.S. Cl.
CPC ............ *G01J 1/42* (2013.01); *G01N 33/4833* (2013.01); *G06K 9/00127* (2013.01); *G06T 7/0016* (2013.01); *G06T 7/194* (2017.01); *G06T 2207/10056* (2013.01); *G06T 2207/30024* (2013.01)

(58) Field of Classification Search
CPC ...... G06K 9/00127; G06T 2207/30024; G06T 2207/30242; G06T 7/004
See application file for complete search history.

(56) References Cited

U.S. PATENT DOCUMENTS

| | | | | |
|---|---|---|---|---|
| 2003/0082818 | A1* | 5/2003 | Bahnson ................. | C12Q 1/24 436/63 |
| 2003/0179916 | A1* | 9/2003 | Magnuson ............... | C12Q 1/24 382/128 |
| 2004/0029213 | A1* | 2/2004 | Callahan ............ | G01N 15/1475 435/40.5 |
| 2005/0276456 | A1* | 12/2005 | Yamato ................ | G02B 21/365 382/128 |
| 2006/0057557 | A1* | 3/2006 | Deutsch ............. | G01N 21/0303 435/4 |
| 2008/0075350 | A1* | 3/2008 | Nitta .................. | G01N 15/1475 382/133 |

(Continued)

FOREIGN PATENT DOCUMENTS

| | | |
|---|---|---|
| JP | 4095811 B2 | 6/2008 |
| JP | 5332610 B2 | 11/2013 |

*Primary Examiner* — Jonathan S Lee
(74) *Attorney, Agent, or Firm* — Muncy, Geissler, Olds & Lowe, P.C.

(57) ABSTRACT

The present invention relates to a cell peeling recognizing device and a cell peeling recognizing method.

When a moving part (robot 6) moves culture vessel 5, imaging device 14 images an interior of culture vessel 5 a plurality of times as the cells move inside the culture vessel due to the moment of inertia, and recognizing part 10*a* recognizes the peeled state of cells C by comparing various sets of the captured imaging data. The peeled state of cells in the culture vessel can be determined with high precision.

3 Claims, 7 Drawing Sheets

(56) References Cited

U.S. PATENT DOCUMENTS

| | | | |
|---|---|---|---|
| 2008/0201083 A1* | 8/2008 | Hata | G06T 7/0012 |
| | | | 702/21 |
| 2008/0279441 A1* | 11/2008 | Matsuo | G01N 15/1475 |
| | | | 382/133 |
| 2009/0081769 A1* | 3/2009 | Kiyota | C12Q 1/02 |
| | | | 435/288.7 |
| 2009/0087075 A1* | 4/2009 | Kii | G02B 21/06 |
| | | | 382/133 |
| 2009/0169089 A1* | 7/2009 | Hunt | G06K 9/00127 |
| | | | 382/133 |
| 2009/0304257 A1* | 12/2009 | Ohjo | C12M 41/46 |
| | | | 382/133 |
| 2012/0092478 A1* | 4/2012 | Honda | C12M 41/14 |
| | | | 348/79 |
| 2012/0214150 A1* | 8/2012 | Kiyota | C12M 27/16 |
| | | | 435/3 |
| 2013/0210130 A1* | 8/2013 | Larcher | C12M 23/44 |
| | | | 435/288.7 |
| 2014/0050386 A1* | 2/2014 | Humayun | A61L 27/38 |
| | | | 382/133 |

* cited by examiner

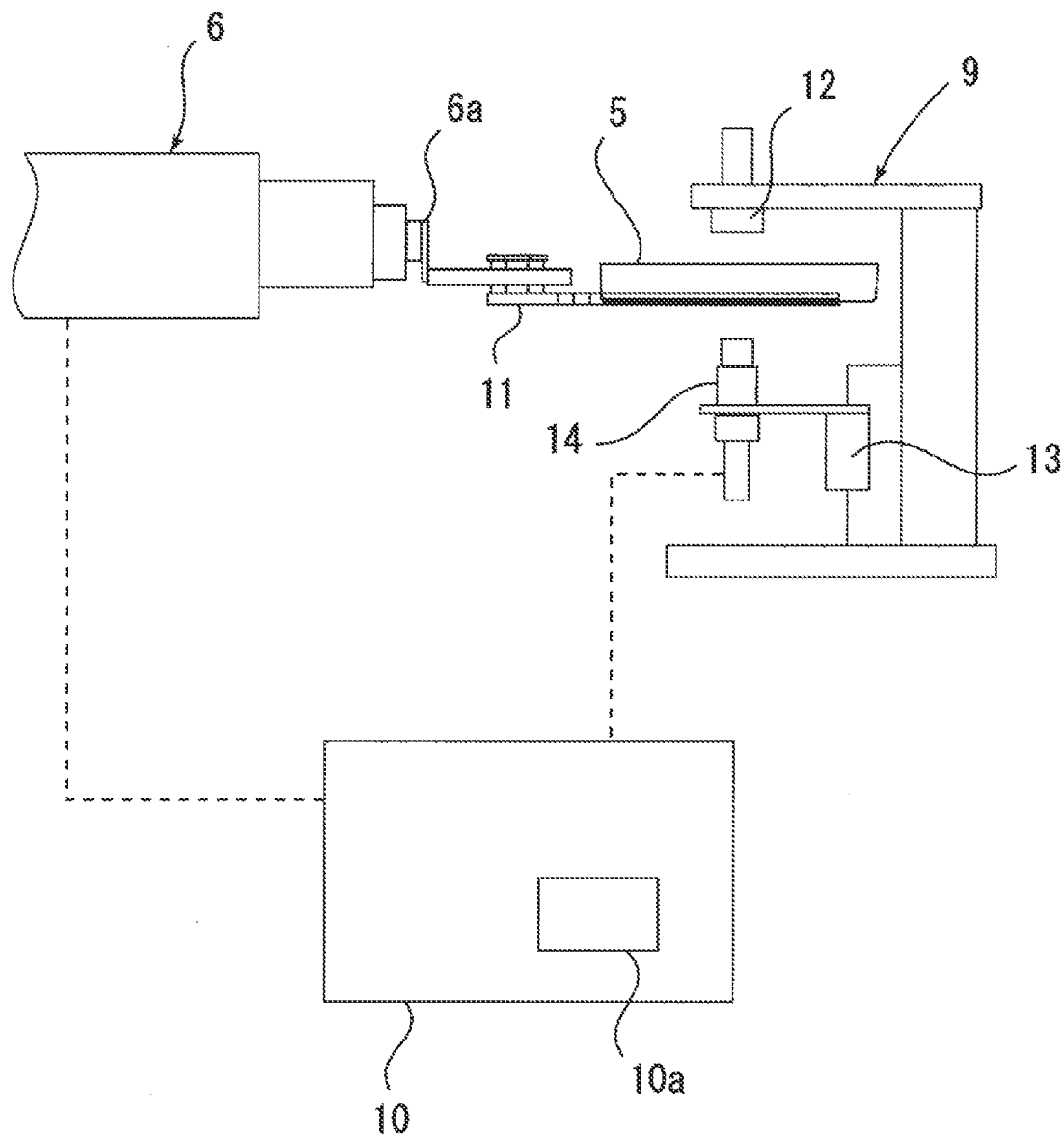

CELL PEELING IDENTIFICATION DEVICE AND CELL PEELING IDENTIFICATION METHOD

CROSS REFERENCE

The present application is related to, claims priority from and incorporates by reference Japanese Patent Application No. 2014-223571, filed on Oct. 31, 2014.

TECHNICAL FIELD

The present invention relates to a cell peeling recognizing device and a cell peeling recognizing method, and, more specifically, to a cell peeling recognizing device and a cell peeling recognizing method in which cells in a culture vessel are imaged and the peeled state of cells in the culture vessel is recognized.

BACKGROUND

When cells cultured in a culture vessel are collected, the cells adhering to the bottom of the culture vessel have to be peeled using a peeling agent such as trypsin. In order to recognize the peeled state of the cells at this time, a cell peeling recognizing method is used in which cells in the culture vessel to which the peeling agent has been added are imaged and the peeled state of the cells in the culture vessel is recognized on the basis of captured imaging data.

In Patent Document 1, a phase-contrast microscope is used to clarify the distinction between cells and the background in the imaging data. Because the brightness is increased when the phase difference of the peripheral portion of cells is increased by cell peeling, peeled cells are identified when the bright component exceeds a predetermined threshold value.

In Patent Document 2, because the area of the cells adhering to the culture vessel is decreased by peeling of the peripheral portion of cells previously adhering to the bottom of the culture vessel, peeled cells are identified when the area of the portion of the cells adhering to the bottom of the culture vessel is determined from captured images of the cells in the imaging data and the area has fallen below a predetermined threshold value.

RELATED ARTS

Patent Documents

[Patent Document 1] Japanese Patent No. 5,332,610
[Patent Document 2] Japanese Patent No. 4,095,811

However, in the recognition methods of Patent Document 1 and Patent Document 2, static images are taken of the cultured cells in a stationary culture vessel, and peeling of cells is estimated on the basis of peeling of a predetermined portion of the cells. However, recognition on this basis is still inaccurate.

In light of this problem, it is an object of the present invention to provide a cell peeling recognizing device and cell peeling recognizing method which are able to more accurately recognize the peeled state of cells.

SUMMARY

A cell peeling recognizing device in claim 1 having an imaging part for imaging an interior of a culture vessel containing culture cells and a recognizing part for recognizing a peeled state of cells in the culture vessel on the basis of imaging data captured by the imaging part, the cell peeling recognizing device, includes a moving part that moves the culture vessel and that accelerates or decelerates or stops the culture vessel in an imaging range of the imaging part. Wherein, the imaging device images the interior of the culture vessel a plurality of times as the cells move inside the culture vessel due to the moment of inertia, and the recognizing device recognizes the peeled state of the cells by comparing various sets of the captured imaging data.

A cell peeling recognizing method in claim 3 for imaging an interior of a culture vessel containing culture cells and recognizing a peeled state of cells in the culture vessel on the basis of imaging data captured by the imaging part, the cell peeling recognizing method, includes moving the culture vessel and accelerating or decelerating or stopping the culture vessel in an imaging range of the imaging part; imaging the interior of the culture vessel a plurality of times as the cells move inside the culture vessel due to the moment of inertia; and recognizing peeled state of the cells by comparing various sets of the captured imaging data.

In the invention according to claims 1 and 3, when the culture vessel is accelerated or decelerated its moving speed or stopped in the imaging range, cells that have been peeled from the culture vessel move inside the culture vessel due to the moment of inertia but cells that have not been peeled from the culture vessel cannot move inside the culture vessel.

Therefore, by imaging the interior of the culture vessel a plurality of times and comparing the various sets of captured imaging data, cells that have moved due to peeling can be reliably recognized and the peeled state of cells can be determined with high precision.

BRIEF DESCRIPTIONS OF THE DRAWINGS

FIG. 1 is a front view of the automated cell culturing system in an example of the present invention.

FIG. 2 (a) and FIG. 2 (b) show a culture vessel containing cells. In FIG. 2 (a), the cells are adhering to the bottom of the culture vessel. In FIG. 2 (b), the cells are peeled.

FIG. 3 (a) and FIG. 3 (b) show an attachment used to move a culture vessel. FIG. 3 (a) is a plan view, and FIG. 3 (b) is a cross-sectional view from b-b in FIG. 3 (a).

FIG. 4 (a) and FIG. 4 (b) show a warming unit and a tapping part. FIG. 4 (a) is a side view, and FIG. 4 (b) is a plan view of the tapping part.

FIG. 5 is a side view of the inspecting part.

DETAILED DESCRIPTION OF EMBODIMENTS

Figure 1:
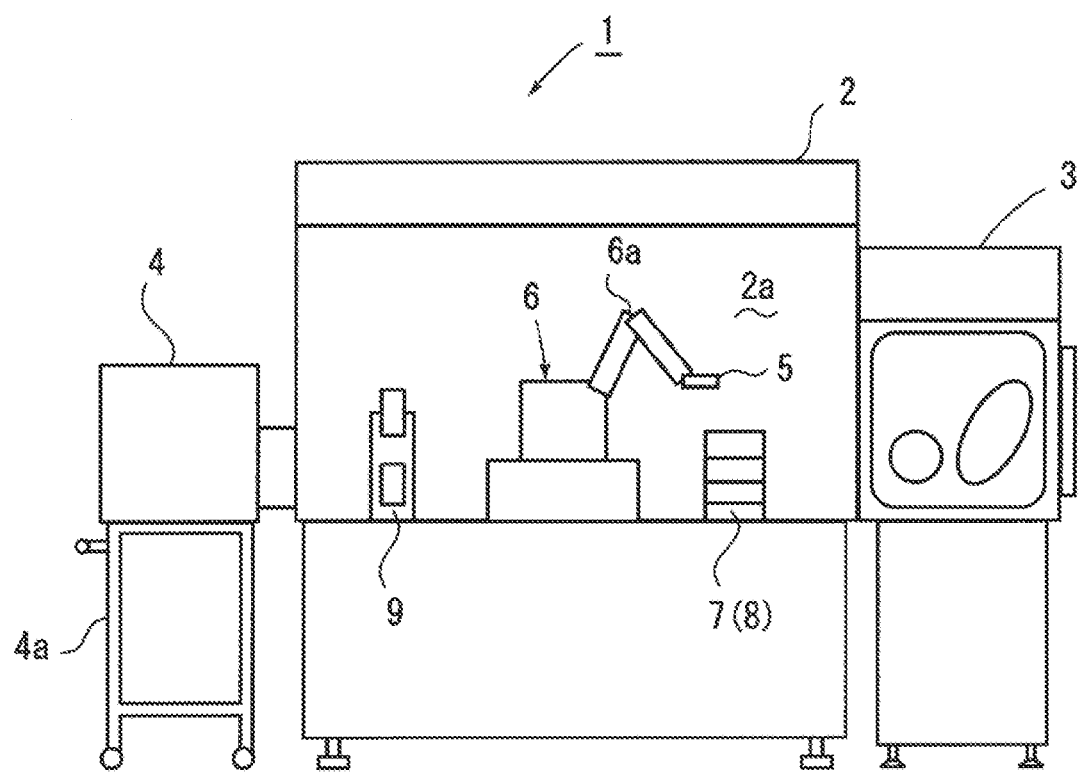

The following is an explanation of the example shown in the drawings. FIG. 1 is a front view of the automated cell culturing system 1 in the example of the present invention. In this automated cell culturing system 1, a working chamber 2a formed inside the system includes an isolator 2 kept in a sterile state, a pass box 3 for introducing tools and instruments to the working chamber 2a, and an incubator 4 for culturing cells which are passed to and from the working chamber 2a.

In the automated cell culturing system 1 in the present example, the culturing operations such as medium replacement and collection are automated, and the system includes the cell peeling recognizing device of the present invention which is able to recognize the peeled state of cells C inside culture vessels 5.

For this purpose, the working chamber 2a in the isolator 2 includes a robot 6 serving as the moving part for moving culture vessels 5, a warming unit 7 for warming culture vessels 5 containing cells C, a tapping part 8 provided in the warming unit 7 for vibrating the culture vessels 5, and an inspecting part 9 for inspecting cells C inside a culture vessel 5 and recognizing cells C in a peeled state. These units are all controlled by a control part 10 (see FIG. 5). Other parts needed to perform culturing operations are provided inside the isolator 2, but explanation of these part has been omitted. Explanation of operations other than those performed to recognize cells C in a peeled state has also been omitted.

The working chamber 2a formed inside the isolator 2 is decontaminated beforehand using a decontaminating gas (hydrogen peroxide gas), and then kept in a sterile state by the supply of pure air.

Gloves (not shown) are provided in a side surface of the isolator 2, which are worn by the operator when performing operations inside the working chamber 2a.

A pass box 3 is provided on the outer right-hand surface of the isolator 2. The working chamber 2a of the isolator 2 and the interior of the pass box 3 are connected via a door (not shown). This enables tools and instruments placed in the pass box 3 from outside to be introduced to the working chamber 2a of the isolator 2.

The incubator 4 can house a plurality of culture vessels 5, and the interior is kept at the optimum temperature and humidity for culturing cells. A dolly 4a provides mobility so that the cells C can be cultured at a location separate from the isolator 2.

When the cells C have been cultured, the isolator 2 and the incubator 4 are connected via a connecting part, the door in the connecting part is opened, and the culture vessels 5 can be passed between the isolator 2 and the incubator 4 in a sterile state.

Figure 2A:
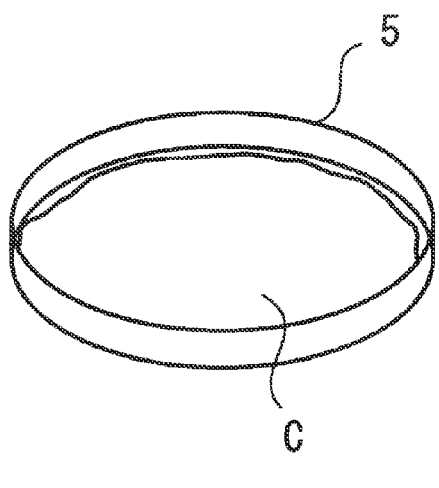
Figure 2B:
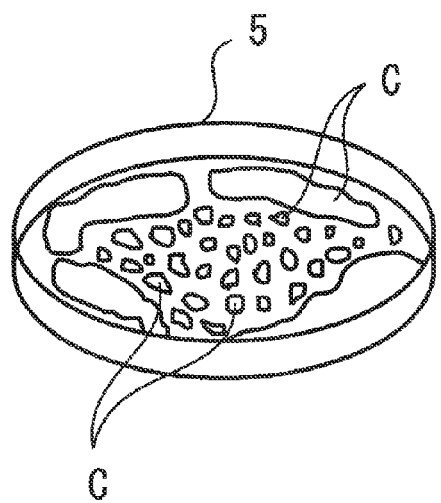

FIG. 2 (*a*) and FIG. 2 (*b*) show a culture vessel 5. Here, the culture vessel 5 is a round dish-like vessel with a shallow bottom. The cells C cultured in the culture vessel 5 can be human cells C such as tissue cells or blood cells.

In FIG. 2 (*a*), the cells C are adhering to the bottom surface of the culture vessel 5. When cells C are cultured in the incubator 4, the cultured cells C adhere to the bottom surface of the culture vessel 5 making the cells C difficult to collect.

In FIG. 2 (*b*), the cells C adhering to the bottom surface of the culture vessel 5 in FIG. 2 (*a*) have been peeled. The cells C were peeled from the culture vessel 5 by introducing a predetermined amount of trypsin into the culture vessel 5 shown in FIG. 2 (*a*), warming the vessel in the warming unit 7 for a predetermined amount of time, and then vibrating the culture vessel 5 with the tapping part 8. As shown in FIG. 2 (*b*), the peeled cells C are finely divided and float in the culture medium.

In order to supply trypsin to a culture vessel 5 containing cells C, a pipette containing trypsin is placed inside the working chamber 2a beforehand, and manipulated by an operator wearing gloves or a robot 6.

Alternatively, a trypsin dispensing part can be provided inside the working chamber 2a, and a robot 6 can move the culture vessel 5 over to the trypsin dispensing part.

The robot 6 can be an articulated industrial robot having an arm 6a composed of a plurality of shafts, and a gripper 6b attached to the end of the arm 6a. These components are protected from the decontaminating gas.

Figure 3A:
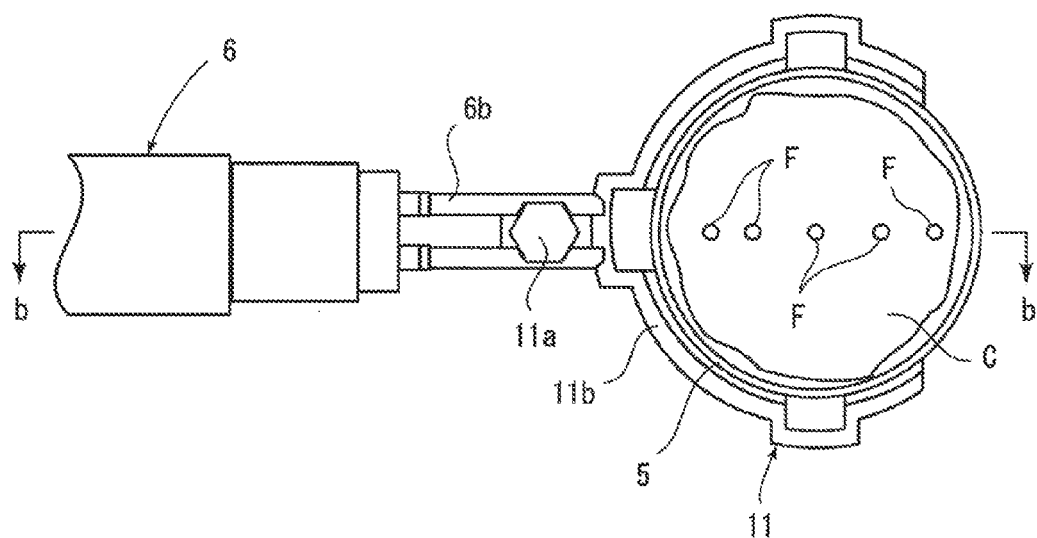
Figure 3B:
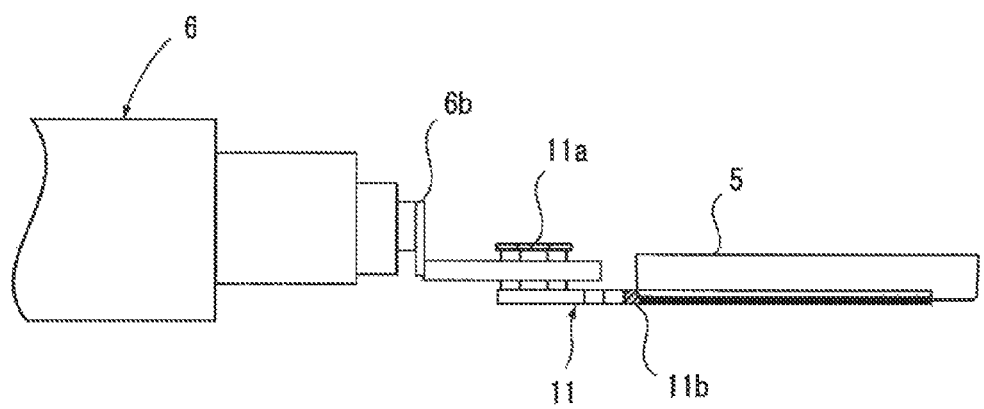

The robot 6 transports a culture vessel 5 using the attachment 11 shown in FIG. 3 (*a*) and FIG. 3 (*b*). FIG. 3 (*a*) is a plan view of the culture vessel 5 and the attachment 11, and FIG. 3 (*b*) is a cross-sectional view from b-b in FIG. 3 (*a*). The attachment 11 includes a grip 11a gripped by the gripper 6b on the robot 6, and a holder 11b for supporting the culture vessel 5.

The holder 11b is a U-shaped component, and the grip 11a is provided on the base of the U-shaped component. A predetermined gap is formed at the tip. The holder 11b has an L-shaped cross-sectional profile in the circumferential direction, and the culture vessel 5 is supported by the bottom surface portion and the side surface portion.

Figure 4A:
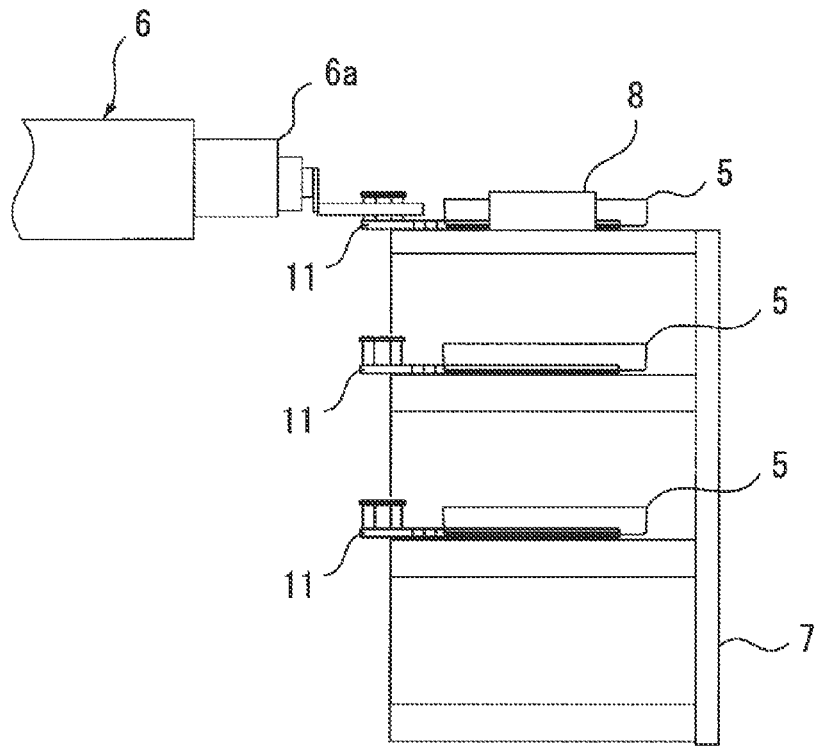
Figure 4B:
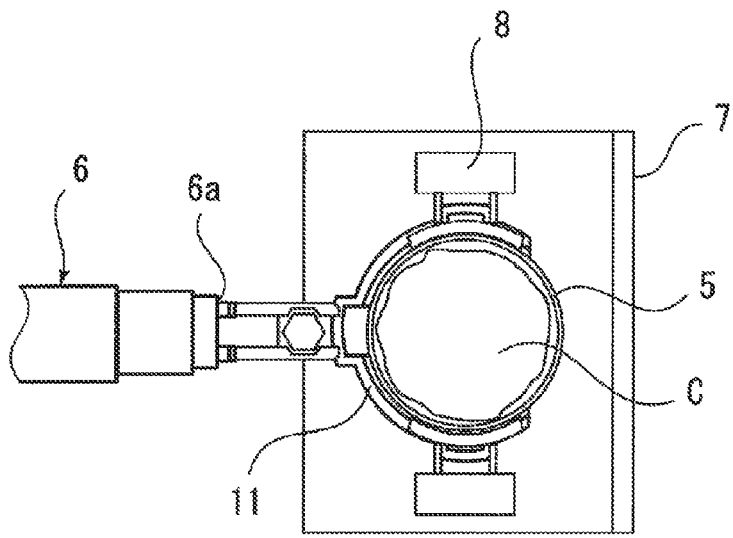

FIG. 4 (*a*) and FIG. 4 (*b*) show the warming unit 7 and the tapping part 8. FIG. 4 (*a*) is a side view, and FIG. 4 (*b*) is a plan view of the tapping part 8. The tapping part 8 is provided on the highest level of the warming unit 7.

Each level of the warming unit 7 is heated by a heating part (not shown). Each culture vessel 5 is placed on an attachment 11, and the culture vessels 5 are warmed to a predetermined temperature.

The tapping part 8 vibrates the culture vessel 5 back and forth by impacts from tappers (or hitting weights), which are provided on both sides of the culture vessel 5 and activated to shuttle by, for example, an air cylinder.

The culture vessel 5 placed on the tapping part 8 has received trypsin and has been warmed for a predetermined amount of time in the warming unit 7, so the trypsin combined with vibration of the culture vessel 5 reduces the adhesive force and peels cells from the bottom surface of the culture vessel 5.

FIG. 5 shows the inspecting part 9, and the inspecting part 9 includes a lighting part 12 held by a holding part, and an imaging part 14 provided so that it can be raised and lowered under the light by a lifting part 13.

The imaging part 14 is connected to a control part 10, and the control part 10 includes a recognizing part 10a for processing imaging data captured by the imaging part 14 to recognize cells C in a peeled state inside a culture vessel 5.

When the robot 6 moves a culture vessel 5 horizontally between the lighting part 12 and the imaging part 14, light from the lighting part 12 passes through the culture vessel 5, and the imaging part 14 images the interior of the culture vessel 5.

Images captured by the imaging part 14 are sent to the recognizing part 10a in the control part 10, and the recognizing part 10a converts the captured images into imaging data composed of a plurality of pixels using any commonly used method.

In the preset example, cells C inside a culture vessel 5 are imaged in the following manner in order to recognize cells C in a peeled state.

First, the robot 6 holds a culture vessel 5 vibrated by the tapping part 8 by the attachment 11, and positions the culture vessel 5 in the illuminated area between the lighting part 12 and the imaging part 14.

The imaging fields F of the imaging part 14 are smaller than the surface area of the culture vessel 5 so that robot 6 can, for example, move the culture vessel 5 continuously in a linear direction so that the five locations arranged linearly are sequentially placed inside the imaging fields F as shown in FIG. 3 (*a*).

When the robot 6 has placed each required position in the culture vessel 5 in the imaging fields F of the imaging part 14, the culture vessel 5 is stopped. Immediately after the culture vessel 5 has been stopped, the cells C peeled from the culture vessel 5 and floating inside the culture vessel 5 continue to move due to the law of inertia.

The imaging part 14 takes a plurality of images, for example, at 0.5-second intervals after the robot 6 has stopped moving the culture vessel 5 and while the cells C inside the culture vessel 5 are moving due to the moment of inertia. Images can be taken three or more times.

As shown in FIG. 3 (*a*), the imaging positions are arranged in linear fashion and, as the culture vessel 5 is moved in a linear direction, it is intermittently accelerated, decelerated moving speed and stopped.

In this way, the cells C do not remain stationary but continue to move. Because the spots located in the imaging fields F are arranged linearly, the direction of the inertia acting on the cells C inside the culture vessel 5 remains constant, and image recognition using the imaging data is easy.

When the captured images are converted into image data composed of a plurality of pixels, the recognizing part 10*a* compares sets of captured imaging data to recognize cells C in a peeled state. The image data in FIG. 6 and FIG. 7 used in the following explanation has been simplified for explanatory purposes.

Figure 6:
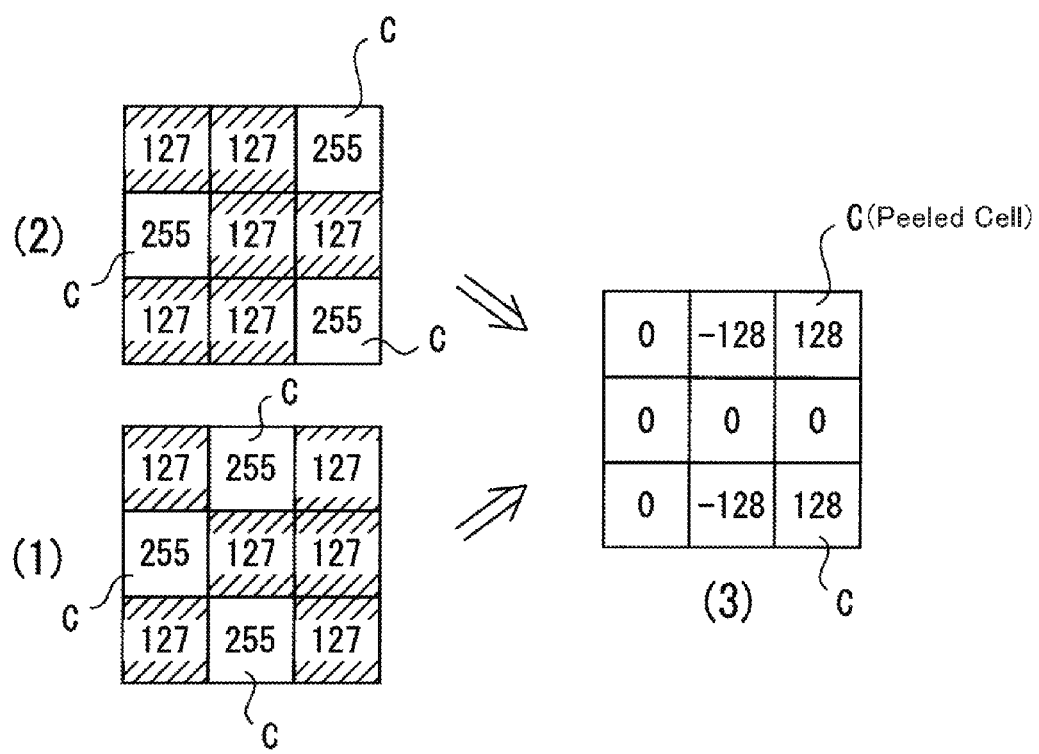
FIG. 6 is a diagram used to explain the first recognition procedure performed by the recognizing part.
Figure 7:
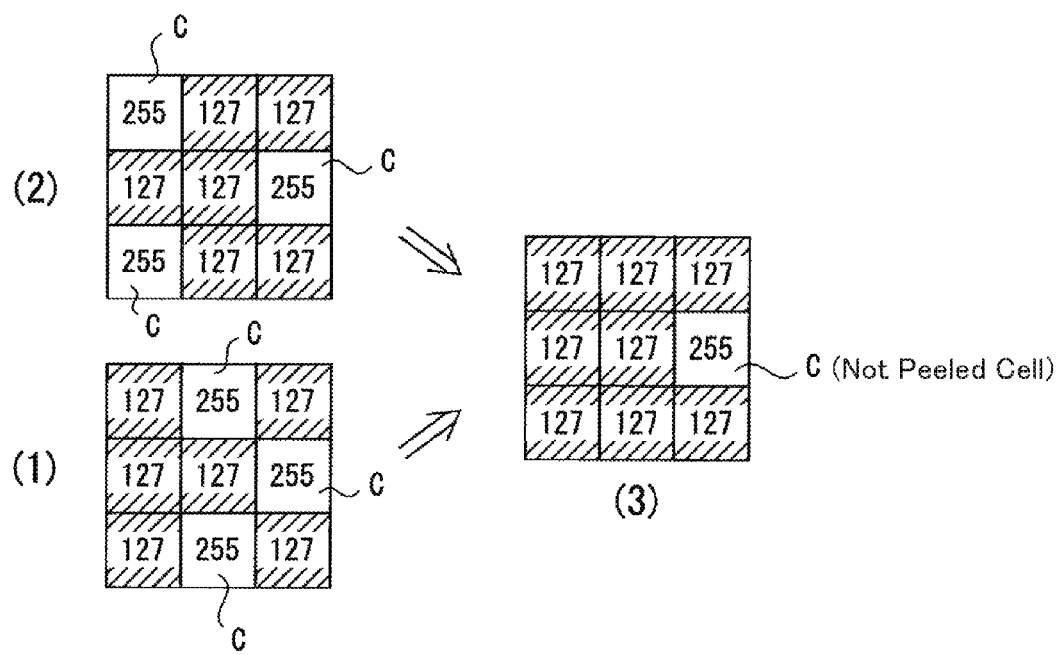
FIG. 7 is a diagram used to explain the second recognition procedure performed by the recognizing part.

In FIG. 6 and FIG. 7, (1) and (2) are sets of image data converted on the basis of two images captured at different times. These images were taken by the imaging part 14 after the culture vessel 5 had been stopped and while the cells C continued to move due to the moment of inertia.

More specifically, the image data is composed of a plurality of pixels, and pixels recognized as cells and pixels recognized as being something other than cells are recognized by their different level of brightness.

When each pixel is displayed, for example, using 256-tone grayscale brightness, pixels where cells C are located are white pixels having a brightness value of 255, and pixels forming the background are gray pixels having a brightness value of 127.

Here, (3) is image data created when the recognizing part 10*a* recognizes cells C in a peeled state on the basis of the recognition method described below. The image shown in (3) does not actually have to be created as long as the processing described below is performed inside the recognizing part 10*a*.

Initially, in the first recognition method shown in FIG. 6, the brightness of pixels in the same locations in different sets of imaging data is compared, and the movement of cells is grasped and the peeled state of cells recognized from the change in brightness.

More specifically, in this explanation, the recognizing part 10*a* compares the differences in brightness for all pixels in the same locations in imaging data (1) and (2), and creates the imaging data shown in (3).

When a pixel has the same brightness in both (1) and (2), this is recognized as '0' in (3). More specifically, in the left-hand columns in the examples, the pixels with a brightness value of '255' indicate cells C, and the pixels with a brightness value of '127' immediately above and below indicate the background. In each case, the difference in brightness in (3) is recognized as '0'.

In contrast, the two pixels with a brightness value of '255' positioned above and below the center pixel in the middle column of (1) indicating cells C change to pixels with a brightness value of '127' in (2) indicating the background because the cells C have moved into the right-hand column. Therefore, the difference in brightness in (3) is recognized as '−128'.

The pixels with a brightness value of '127' positioned above and below the center pixel in the right-hand column of (1) indicating the two background change to pixels with a brightness value of '255' in (2) because the cells C have moved into these pixels. Therefore, the difference in brightness in (3) is recognized as '128'.

When the imaging data in (3) has been created in this manner, the recognizing part 10*a* recognizes that the pixels with a difference in brightness of '128' in the imaging data in (3) are cells C that have become peeled from the culture vessel 5 and have moved due to the moment of inertia. The recognizing part 10*a* counts the number of pixels in the imaging data of (3) indicating cells C that have become peeled and have moved, and multiplies this by the area per pixel to calculate the area with peeled cells.

Next, in the second recognition method shown in FIG. 7, in a comparison of the brightness of pixels in the same locations in different sets of imaging data similar to the first recognition method, pixels recognized as cells are extracted from pixels whose brightness has not changed, and the cells C located in these pixels are determined to be unpeeled.

More specifically to be explained, the recognizing part 10*a* compares the differences in brightness for all pixels in the same locations in imaging data (1) and (2), selects the darker pixel, and creates the imaging data shown in (3).

In other words, pixels with the same brightness in both (1) and (2) have the same brightness in (3). Specifically, in the right-hand columns in the examples, the pixels with a brightness value of '255' indicate cells C, and the pixels with a brightness value of '127' immediately above and below indicate the background. For these pixels, the same brightness is used in (3).

In contrast, in the middle columns in (1), the pixels with a brightness value of '255' immediately above and below the center indicate cells C, but these cells C move to the left-hand column in (2) so these pixels change to pixels having a brightness value of '127' indicating the background. Therefore, in (3), these pixels are recognized as pixels having a darker brightness value of '127'.

In the left-hand columns in (1), the pixels with a brightness value of '127' immediately above and below the center indicate the background, but cells C move into the left-hand column in (2) so these pixels change to pixels having a brightness value of '255'. Therefore, in (3), these pixels are recognized as pixels having a darker brightness value of '127'.

When the imaging data in (3) has been created in this manner, the recognizing part 10*a* recognizes that the pixel with a brightness of '255' in the imaging data in (3) as a cell C that has not become peeled from the culture vessel 5.

The recognizing part 10*a* counts the number of pixels in the imaging data of (3) indicating cells C that have not become peeled, and multiplies this by the area per pixel to calculate the area with unpeeled cells.

Also, the area with peeled cells determined using the first recognition method can be added to the area with unpeeled cells determined using the second recognition method, and the area with peeled cells can be divided by the total area with cells to determine the cell peeling rate.

Then, the recognizing part 10*a* calculates the peeling rate for all of the imaging fields F in the culture vessel 5 on the basis of the first and second recognition methods, and calculates the peeling rate for the entire culture vessel 5 from the peeling rates of each imaging field F. For example, the average peeling rate of the five imaging positions can be used as the peeling rate for the entire culture vessel 5.

When imaging has been performed three times at each imaging position, the peeling rates can be respectively calculated by comparing the first image to the second image and the second image to the third image.

The peeling rate obtained in this manner can serve as an index for determining the optimum amount of trypsin to be added, the optimum retention time, and the optimum number of vibrations required for each type of cell C.

The peeling rates determined on the basis of the cell peeling recognizing method in the present example enables peeled and moving cells C and unpeeled and stationary cells C to be recognized reliably because the culture vessel 5 is stopped and the cells C inside the vessel move due to the moment of inertia. As a result, the peeled state of cells C can be recognized with a high degree of precision.

In contrast to the above, because the recognition method of the prior art observes cells without moving the culture vessel 5, the cells C inside the vessel do not move. Therefore, only some are peeled and mistakes are made in determining how many cells C are not completely peeled.

Although it depends on the target cells C, even when cells C moving inside the culture vessel 5 have to be recognized across a plurality of pixels in the imaging data, the imaging interval of the imaging part 14 can be adjusted so that there is no overlap in the positions of moving cells C in the first and second image data and so that highly precise recognition can be performed.

The moving part is not limited to a robot 6. Any moving part can be used as long as the culture vessel 5 can be moved and can be accelerated or decelerated moving speed or stopped in the imaging fields F of the imaging part 14.

In the example described above, a robot 6 stopped the culture vessel 5 in the imaging fields F of the imaging part 14 and the cells C moved due to the moment of inertia. However, the moving culture vessel 5 can be accelerated or decelerated moving speed in order to cause the cells C to move due to the moment of inertia. In other words, as long as cells C moving due to the moment of inertia can be imaged, the culture vessel 5 does not have to be stopped.

For example, after moving the culture vessel 5 towards the inspecting part 9 at a predetermined speed, the robot 6 can decelerate once the imaging fields F of the imaging part 14 have been reached so that the cells C in the culture vessel 5 can continue moving due to the moment of inertia.

Afterwards, the robot 6 can move the culture vessel 5 through the imaging fields F of the imaging part 14 at a constant speed while the imaging part 14 images the interior of the culture vessel 5 several times. The sets of imaging data can then be superimposed by the recognizing part 10a using a commonly used technique such as pattern matching to recognize the cells C moving through the culture vessel 5 due to the moment of inertia.

In another method for moving peeled cells C through a culture vessel 5, the culture vessel 5 can be suddenly stopped in the imaging fields. The culture vessel 5 can then just as suddenly start to move and accelerate, allowing the cells C to move further due to the moment of inertia. The tapping part used to vibrate the culture vessel 5 can also be provided in the imaging range, and cells C can be caused to move due to the moment of inertia by accelerating and stopping the vibrations caused by tapping.

A plurality of imaging part can be provided, cells C moving due to the moment of inertia caused by acceleration and vibrations can be imaged in the imaging range of one imaging part, and cells C moving due to the moment of inertia caused by deceleration and stopping can be imaged in the imaging range of another imaging part. In this way, the interior of the culture vessel 5 can be imaged more than once.

In each case and for whatever reason, when the culture vessel 5 is accelerated or decelerated moving speed or stopped, the cells C inside the culture vessel 5 are moved using inertia, and the interior of the culture vessel 5 is imaged more than once to capture peeled cells C before and after the movement.

The invention claimed is:

1. A cell peeling recognizing method for imaging an interior of a culture vessel containing culture cells and recognizing a peeled state of cells in the culture vessel on the basis of imaging data captured by an imaging part, the cell peeling recognizing method, comprising:
   repeatedly moving the culture vessel in a linear direction to sequentially locate multiple spots of the culture vessel within an imaging range of the imaging part by accelerating or decelerating a moving speed of all of the multiple spots of the culture vessel or stopping the culture vessel in the imaging range of the imaging part;
   imaging the interior of the culture vessel a plurality of times while the cells are moving inside the culture vessel due to the moment of inertia that is generated by one of the acceleration, the deceleration and the stopping of the culture vessel; and
   recognizing peeled state of the cells by comparing various sets of the captured imaging data that are captured at all of the multiple spots of the culture vessel.

2. The cell peeling recognizing method according to claim 1, wherein
   the captured data is composed of a plurality of pixels, the pixels recognized as cells and the pixels recognized as extracellular sections being recognized by difference in brightness,
   the brightness of pixels in the same locations in the various sets of captured imaging data are compared, and
   the movement of cells is grasped and the peeling state of cells is recognized from changes in brightness.

3. The cell peeling recognizing method according to claim 2, wherein
   the pixels recognized as cells are extracted from pixels experiencing no change in brightness in the brightness comparison of the various sets of the captured imaging data.

* * * * *